United States Patent [19]

Tsushima et al.

[11] Patent Number: 5,006,538
[45] Date of Patent: Apr. 9, 1991

[54] CERTAIN INSECTICIDAL 6-(PHENOXY-2-PYRIDYL)-METHYL-NEO-PHENTAL ETHERS

[75] Inventors: Kazunori Tsushima, Nishinomiya; Noritada Matsuo, Itami; Hirosi Kisida, Takarazuka; Toshihiko Yano, Ashiya, all of Japan

[73] Assignee: Sumitomo Chemical Company, Limited, Osaka, Japan

[21] Appl. No.: 264,865

[22] Filed: Oct. 31, 1988

[30] Foreign Application Priority Data

Nov. 7, 1987 [JP] Japan ............... 62-281834
Jun. 7, 1988 [JP] Japan ............... 63-141170

[51] Int. Cl.$^5$ ............... C07D 213/64; A01N 43/40
[52] U.S. Cl. ............... 514/345; 546/301; 546/302
[58] Field of Search ............... 546/301, 302; 514/345

[56] References Cited

U.S. PATENT DOCUMENTS 4,664,698  5/1987  Tsushima et al. ............... 71/94

FOREIGN PATENT DOCUMENTS 0175377  3/1986  European Pat. Off. ............... 546/302
0240978  10/1987  European Pat. Off. ............... 71/94
0266891  5/1988  European Pat. Off. ............... 546/302
1570982  7/1980  United Kingdom ............... 568/52
2184439  6/1987  United Kingdom ............... 546/302

Primary Examiner—Alan L. Rotman
Attorney, Agent, or Firm—Stevens, Davis, Miller & Mosher

[57] ABSTRACT

An ether compound represented by the following formula (I), it production and insecticidal compositions containing it as an active ingredient:

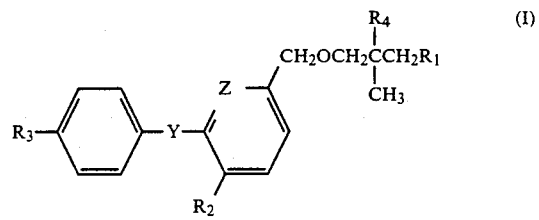

wherein $R_1$, represents a halogen atom or a methyl group; $R_2$ represents a hydrogen atom or a fluorine atom; $R_3$ represents a hydrogen atom, a halogen atom or a methyl group; $R_4$ represents a ($C_1$–$C_3$)alkyl group; Y represents an oxygen atom, a sulfur atom, a methylene group or —NH—; and Z represents a nitrogen atom or —CH=.

6 Claims, No Drawings

CERTAIN INSECTICIDAL 6-(PHENOXY-2-PYRIDYL)-METHYL-NEOPHENTAL ETHERS

The present invention relates to a novel ether compound, a method for producing it and its use as an insecticide.

Hitherto, insecticidal compounds having an ether structure are described in B.P. No. 1,570,982, U.S. Pat. No. 4,664,698, etc.

These compounds, however, may not always be said to be quite satisfactory in the insecticidal activity.

In view of such situation, the present inventors extensively studied to develop a compound having excellent insecticidal activity, and as a result, have found that the novel ether compound of the present invention is excellent insecticidal compound. The present inventors have thus attained to the present invention.

The present invention provides an ether compound represented by the formula (I),

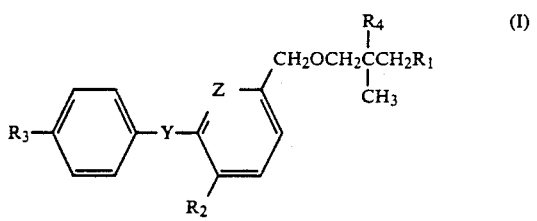

wherein $R_1$ represents a halogen atom or a methyl group, $R_2$ represents a hydrogen or fluorine atom, $R_3$ represents a hydrogen or halogen atom or a methyl group, $R_4$ represents a $C_1$-$C_3$ alkyl group, Y represents an oxygen or sulfur atom, a methylene group or a group represented by —NH—, and Z represents a nitrogen atom or a group represented by —CH=, a method for producing it, insecticides containing it as an active ingredient and a method for killing insects with it.

As specific examples of insects against which the present compounds are particularly efficacious, there are mentioned Hemiptera such as planthoppers, leafhoppers, aphides, bugs, etc.; Lepidoptera such as armyworms and cutworms, etc.; Diptera such as common mosquito (*Culex pipiens pallens*), housefly (*Musca domestica*), etc.; Dictyoptera such as German cockroach (*Blattella germanica*), etc.; and Coleoptera, Orthoptera, Isoptera, etc.

Among the present compounds, preferred ones are those in which $R_3$ is a hydrogen, chlorine, bromine or fluorine atom or a methyl group, $R_4$ is a methyl or ethyl group and Y is an oxygen atom or a group represented by —NH—. And, among these compounds, more preferred ones are those in which $R_3$ is a hydrogen atom, $R_4$ is a methyl or ethyl group and Y is an oxygen atom, and those in which $R_3$ is a hydrogen atom, $R_4$ is a methyl or ethyl group, Y is a group represented by —NH— and Z is a group represented by —CH=.

Particularly, preferred compounds are as follows:
6-Phenoxy-2-pyridylmethyl 3-chloro-2,2-dimethylpropyl ether
6-Phenoxy-2-pyridylmethyl 2,2-dimethylbutyl ether
6-Phenoxy-2-pyridylmethyl 2-ethyl-2-methylbutyl ether
4-Fluoro-3-anilinobenzyl 2,2-dimethylbutyl ether
4-Fluoro-3-phenoxybenzyl 2,2-dimethylbutyl ether
4-Fluoro-3-anilinobenzyl 2-ethyl-2-methylbutyl ether
5-Fluoro-6-phenoxy-2-pyridylmethyl 2,2-dimethylbutyl ether, etc.

Next, a method for producing the present compounds will be shown.

METHOD A

The present compounds are produced by reacting a compound represented by the formula (II),

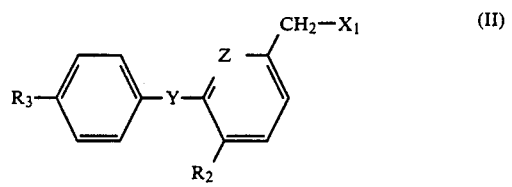

wherein $R_2$, $R_3$, Y and Z represent the same meanings as described above, and $X_1$ represents a halogen atom, with a compound represented by the formula (III),

wherein $R_1$ and $R_4$ represent the same meanings as described above.

This reaction is usually carried out in a solvent in the presence of a base. The solvent includes N,N-dimethylformamide (DMF), dimethyl sulfoxide (DMSO), 1,3-dimethyl-2-imidazolidinone, ether solvents [e.g. tetrahydrofuran (THF), 1,4-dioxane, dimethoxyethane (DME)], hydrocarbon solvents (e.g. benzene, toluene, hexane), water, etc., and the base includes the hydrides, hydroxides and alkoxides of alkali metals and alkyl lithium, etc. The reaction time is usually from 1 to 72 hours, and the reaction is carried out at room temperature or under heating. If necessary, there may be used phase transfer catalysts such as Crown ethers, organic quaternary ammonium salts, phosphonium salts, sulfonium salts, etc.

METHOD B

Among the present compounds, those in which $R_1$ is a halogen atom, i.e. compounds represented by the formula (I'),

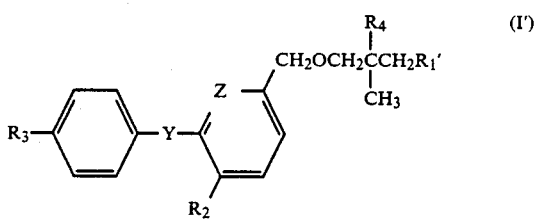

wherein $R_1'$ represents a halogen atom, and $R_2$, $R_3$, $R_4$, Y and Z represent the same meanings as described above,
can also be produced by reacting a compound represented by the formula (IV),

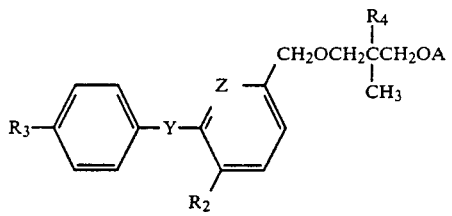

wherein $R_2$, $R_3$, $R_4$, Y and Z represent the same meanings as described above, and A represents a hydrogen atom or a methanesulfonyl or toluenesulfonyl group, with a halogenating reagent.

This reaction is usually carried out in a solvent at room temperature or under heating in from 1 to 72 hours. The solvent includes sulfolane, N-methylpyrrolidone, DMSO, hexamethylphosphoric triamide (HMPA), alcohol solvents (e.g. diethylene glycol, triethylene glycol, tetraethylene glycol), ether solvents (e.g. diethylene glycol dimethyl ether, triethylene glycol dimethyl ether, tetraethylene glycol dimethyl ether), halogenated hydrocarbons (e.g. chloroform, dichloroethane, dichloromethane, carbon tetrachloride, chlorobenzene, bromobenzene), hydrocarbon solvents (e.g. toluene, xylene), etc.

For examples of the halogenating reagent, there are hydrogen halides, halogenated phosphorus compounds (e.g. phosphorus pentachloride, phosphorus trichloride, phosphorus oxychloride, phosphorus oxybromide, triphenylphosphine dihalide), halogenated sulfur compounds (e.g. thionyl chloride), halogenated alkali metals (e.g. potassium fluoride, cesium fluoride, potassium iodide), halogenated alkaline earth metals (e.g. calcium fluoride), etc.

Also in this reaction, Crown ethers may be used if necessary.

METHOD C

Among the present compounds, those in which Y is an oxygen or sulfur atom, Z is a nitrogen atom and $R_1$ is a methyl group, i.e. compounds represented by the formula (I''),

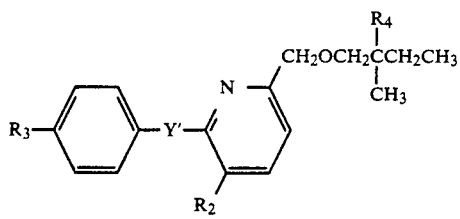

wherein $R_2$, $R_3$ and $R_4$ represent the same meanings as described above, and Y' represents an oxygen or sulfur atom,
can be produced by reacting a compound represented by the formula (V),

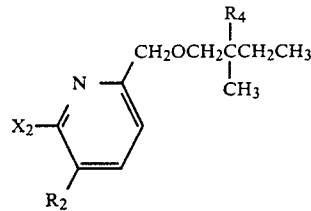

wherein $R_2$ and $R_4$ represent the same meanings as described above, and $X_2$ represents a halogen atom,
with a compound represented by the formula (VI),

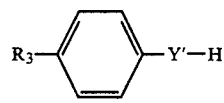

wherein $R_3$ and Y' represent the same meanings as described above.

This reaction is usually carried out in DMF, DMSO, HMPA or a hydrocarbon solvent (e.g. toluene, xylene) or without a solvent in the presence of a base (e.g. the hydrides, hydroxides, carbonates and alkoxides of alkali metals). The reaction time is usually from 1 to 72 hours, and the reaction is carried out under heating. If necessary, phase transfer catalysts (e.g. Crown ethers, organic quaternary ammonium salts, phosphonium salts, sulfonium salts) or catalysts (e.g. copper powder, copper salts) may also be used.

Materials for producing the present compounds such as the compound represented by the formula (II) can be produced according to the method described in U.S. Pat. No. 4,664,698.

When the present compounds are used as an active ingredient for insecticides, they may be used as they are without adding any other ingredients. Usually, however, they are formulated before use into emulsifiable concentrates, wettable powders, dusts, granules, oil sprays, aerosols, heating fumigants (e.g. mosquito coils, electric mosquito mats), foggings, non-heating fumigants, poisonous baits, etc. by mixing with solid carriers, liquid carriers, gaseous carriers, surface active agents, other auxiliaries for formulation, baits, etc. or impregnating into bases such as mosquito coil carriers, mats, etc.

The preparations contain as an active ingredient from 0.01 to 95 wt. % of the present compounds.

The solid carriers include fine powders or granules of kaolin clay, attapulgite clay, bentonite, terra abla, pyrophyllite, talc, diatomaceous earth, calcite, corn stalk powder, walnut shell powder, urea, ammonium sulfate, synthetic hydrated silicon dioxide, etc. The liquid carriers include aliphatic hydrocarbons (e.g. kerosene), aromatic hydrocarbons (e.g. benzene, toluene, xylene, methylnaphthalene), halogenated hydrocarbons (e.g. dichloroethane, trichloroethylene, carbon tetrachloride), alcohols (e.g. methanol, ethanol, isopropanol, ethylene glycol, cellosolve), ketones (e.g. acetone, methyl ethyl ketone, cyclohexanone, isophorone), ethers (e.g. diethyl ether, dioxane, tetrahydrofuran), esters (e.g. ethyl acetate), nitriles (e.g. acetonitrile, isobutyronitrile), acid amides (e.g. dimethylformamide, dimethylacetamide), dimethyl sulfoxide, vegetable oils (e.g. soybean oil, cotton seed oil), etc. The gaseous carriers include freon gas, LPG (liquefied petroleum gas), dimethyl ether, etc. The surface active agents used for emulsification, dispersion, wetting, etc. include anionic surface active agents such as the salt of alkyl sulfates, alkylarylsulfonates, dialkyl sulfosuccinates, the salt of polyoxyethylene alkylaryl ether phosphoric acid esters, naphthalenesulfonic acid/formalin condensates, etc., and nonionic surface active agents such as polyoxyethylene alkyl ether, polyoxyethylene polyoxypropylene block copolymers, sorbitan fatty acid esters, polyoxyethylene sorbitan fatty acid esters, etc. The auxiliaries for formulation such as fixing agents, dispersing agents, etc. include lignosulfonates, alginates, polyvinyl alcohol, gum arabic, molasses, casein, gelatin, CMC (carboxymethyl cellulose), pine oil, agar, etc. The stabilizers include alkyl phosphates [e.g. PAP (isopropyl acid phosphate), TCP (tricresyl phosphate)], vegetable oils, epoxidized oils, the foregoing surface active agents, antioxidants (e.g. BHT, BHA), fatty acid salts (e.g. sodium oleate, calcium stearate), fatty acid esters (e.g. methyl oleate, methyl stearate), etc.

The preparations thus obtained are used as they are or diluted with water. Also, they may be used mixed with other insecticides, acaricides, nematocides, fungicides, herbicides, plant growth regulators, fertilizers, soil improvers, etc.

When the present compounds are used as an insecticide, their dosage rate is usually from 5 to 500 g per 10 ares. When the emulsifiable concentrates, wettable powders, etc. are used diluted with water, the application concentration of the active ingredient is from 10 to 1,000 ppm, and the dusts, granules, oil sprays, aerosols, etc. are applied as they are without being diluted.

Next, the present invention will be illustrated in more detail with reference to the following production examples, formulation examples and test examples, but it is not limited to these examples only.

First, production examples for the present compounds will be shown.

PRODUCTION EXAMPLE 1 PRODUCTION OF PRESENT COMPOUND (1) BY Method A

Under a nitrogen atmosphere, 0.65 g of sodium hydride (60% oily suspension) was suspended in 10 ml of dry DMF, and a solution of 3.23 g of 2-chloromethyl-6-phenoxypyridine and 2.00 g of 3-chloro-2,2-dimethylpropanol in 10 ml of dry DMF was added dropwise with ice-cooling. After stirring for 12 hours at room temperature, the reaction solution was poured into dilute hydrochloric acid-ice water and extracted twice with diethyl ether. The ether layers were combined, washed with a saturated aqueous sodium chloride solution and dried over anhydrous magnesium sulfate, and the solvent was removed under reduced pressure. The residue was subjected to column chromatography on silica gel (developing solvent, hexane : ethyl acetate=50:1) to obtain 0.52 g of desired 6-phenoxy-2-pyridylmethyl 3-chloro-2,2-dimethylpropyl ether [present compound (1)] as a colorless oily product.

$n^{24.0}_D 1.5425$.

$^1$H-NMR data (solvent, CDCl$_3$; internal standard, TMS): $\delta$ (ppm) 1.01 (s, 6H), 3.35 (s, 2H), 3.50 (s, 2H), 4.52 (s, 2H), 6.62–7.82 (m, 8H).

PRODUCTION EXAMPLE 2 PRODUCTION OF PRESENT COMPOUND (23) BY Method A

Procedure was carried out in the same manner as in Production example 1 except that 3.49 g of 2-chloromethyl-5-fluoro-6-phenoxypyridine was used in place of 3.23 g of 2-chloromethyl-6-phenoxypyridine, to obtain 0.71 g of desired 5-fluoro-6-phenoxy-2-pyridylmethyl 3-chloro-2,2-dimethylpropyl ether [present compound (23)] as a colorless oily product.

$n^{25.0}_D 1.5330$.

$^1$-NMR data (solvent, CDCl$_3$; internal standard, TMS): $\delta$ (ppm) 1.02 (s, 6H), 3.35 (s, 2H), 3.51 (s, 2H), 4.52 (s, 2H), 6.65–7.75 (m, 7H).

PRODUCTION EXAMPLE 3 PRODUCTION OF PRESENT COMPOUND (2) BY Method B

Ten grams of potassium fluoride was added to 100 ml of diethylene glycol, and the resulting mixture was heated to from 170° to 190° C. under reduced pressure (100–20 mmHg) to distill away about 50 ml of diethylene glycol. After cooling to room temperature, 1.27 g of 6-phenoxy-2-pyridylmethyl 3-methanesulfonyloxy-2,2-dimethylpropyl ether was added, followed by heating to 200° C. for 3 hours. After cooling, it was poured into ice water and extracted twice with ethyl acetate. The ethyl acetate layers were combined, washed with a saturated aqueous sodium chloride solution and dried over anhydrous magnesium sulfate. The residue was subjected to column chromatography on silica gel (developing solvent, hexane: ethyl acetate=50:1) to collect a fraction corresponding to an Rf value of from 0.7 to 0.8 (silica gel plate, developing solvent; hexane: ethyl acetate=3:1). Further, this fraction was treated by preparative thin layer chromatography (developing solvent, toluene: diethyl ether=20:1) to obtain 146 mg of desired 6-phenoxy-2-pyridylmethyl 3-fluoro-2,2-dimethylpropyl ether [present compound (2)] as an oily product (purity, 83%).

$n^{20.5}_D 1.5309$.

$^1$H-NMR data (solvent, CDCl$_3$; internal standard, TMS): $\delta$ (ppm) 1.00 (bs, 6H), 3.30 (bs, 2H), 4.22 (d, 2H), 4.50 (s, 2H), 6.62–7.86 (m, 8H).

$^{19}$F-NMR data [solvent, CDCl$_3$; external standard, CF$_3$COOH (+76.5 ppm)]: $\delta$ (ppm) +224.3 (bt).

PRODUCTION EXAMPLE 4 PRODUCTION OF PRESENT COMPOUND (7) BY Method B 1.0 Gram of 6-phenoxy-2-pyridylmethyl 3-hydroxy-2,2-dimethylpropyl ether and 3.7 g of triphenylphosphine were dissolved in 15 ml of dry THF, and 2.3 g of carbon tetrabromide was added with ice-cooling, followed by stirring at room temperature for 14 hours. Thereafter, 45 ml of hexane was added to the reaction solution, and the formed insoluble product was removed by filtration. The filtrate was washed with water and then with a saturated aqueous sodium chloride solution and concentrated under reduced pressure. To the residue obtained was added again hexane, the insoluble product was removed by filtration, and the filtrate was concentrated under reduced pressure. The residue obtained was subjected to column chromatography on silica gel (developing solvent, hexane: ethyl acetate=50:1) to obtain 0.77 g of desired 6-phenoxy-2-pyridylmethyl 3-bromo-2,2-dimethylpropyl ether [present compound (7)] as a colorless oily product.

$n^{23.0}_D 1.5545$.

$^1$H-NMR data (solvent, CDCl$_3$; internal standard, TMS): $\delta$ (ppm) 1.02 (s, 6H), 3.31 (s, 2H), 3.40 (s, 2H), 4.49 (s, 2H), 6.60–7.78 m, 8H).

PRODUCTION EXAMPLE 5 PRODUCTION OF PRESENT COMPOUND (17) BY Method A 4.4 Grams of a 45% aqueous sodium hydroxide solution, 100 mg of tetrabutylammonium bromide and 5 ml of toluene were mixed, and to the resulting mixture, a solution of 0.7 g of 2,2-dimethylbutanol and 1.72 g of 2-chloromethyl-6-phenoxypyridine in 10 ml of toluene was added at room temperature under a nitrogen atmosphere. After 12 hours, the reaction solution was poured into hydrochloric acid-ice water and extracted twice with diethyl ether. The ether layers were combined, washed with a saturated aqueous sodium chloride solution and dried over anhydrous magnesium sulfate. The solvent was removed under reduced pressure, and the residue was treated by preparative thin layer chromatography (developing solvent, hexane: ethyl acetate=5:1) to obtain 0.45 g of desired 6-phenoxy-2-pyridylmethyl 2,2-dimethylbutyl ether [present compound (17)] as an oily product.

$n^{21.0}_D 1.5250$.

$^1$H-NMR data (solvent, CDCl$_3$; internal standard, TMS): $\delta$ (ppm) 0.82 (bt, 3H), 0.92 (s, 6H), 1.20–1.55 (m, 2H), 3.24 (s, 2H), 4.51 (s, 2H), 6.65 (bd, 1H), 7.00–7.80 (m, 7H).

PRODUCTION EXAMPLE 6 PRODUCTION OF PRESENT COMPOUND (1) BY Method B 0.5 Gram of 6-phenoxy-2-pyridylmethyl 3-hydroxy-2,2-dimethylpropyl ether was dissolved in 20 ml of dry xylene, and 0.73 g of phosphorus pentachloride was added, followed by heating under reflux for 3 hours. Thereafter, the reaction solution was poured into ice water and extracted with xylene. The xylene layer was washed with water, dried and concentrated. The residue was subjected to column chromatography on silica gel (developing solvent, hexane: ethyl acetate=50:1) to obtain 90 mg of desired 6-phenoxy-2-pyridylmethyl 3-chloro-2,2-dimethylpropyl ether [present compound (1)].

$^1$H-NMR data (solvent, CDCl$_3$; internal standard, TMS): $\delta$ (ppm) 1.00 (s, 6H), 3.32 (s, 2H), 3.48 (s, 2H), 4.51 (s, 2H), 6.60–7.80 (m, 8H).

PRODUCTION EXAMPLE 7 PRODUCTION OF PRESENT COMPOUND (3) BY Method A

Procedure was carried out in the same manner as in Production example 1 except that 4.13 g of 4-fluoro-3-phenoxybenzyl bromide was used in place of 3.23 g of 2-chloromethyl-6-phenoxypyridine, to obtain 3.79 g of desired 4-fluoro-3-phenoxybenzyl 3-chloro-2,2-dimethylpropyl ether [present compound (3)] as a colorless oily product.

$n^{26.0}_D 1.5401$.

$^1$H-NMR data (solvent, CDCl$_3$; internal standard, TMS): $\delta$ (ppm) 1.01 (s, 6H), 3.35 (s, 2H), 3.51 (s, 2H), 4.40 (s, 2H), 6.80–7.45 (m, 8H).

$^{19}$F-NMR data (solvent, CDCl$_3$; external standard, CF$_3$COOH (+76.5 ppm)] $\delta$ (ppm) +129.3 (m).

PRODUCTION EXAMPLE 8 PRODUCTION OF PRESENT COMPOUND (17) BY Method C 1.86 Grams of phenol was dissolved in 10 ml of xylene, and 0.74 g of sodium hydroxide was added. The reaction solution was heated under reflux for 6 hours while water, a by-product, was removed through a column packed with calcium chloride. Thereafter, 3.0 g of 6-chloro-2-pyridylmethyl 2,2-dimethylbutyl ether and 300 mg of cuprous chloride were added, followed by heating under reflux for further 8 hours. After cooling, it was poured into dilute hydrochloric acid-ice water and extracted with xylene. The xylene layer was washed with water and dried, and the solvent was removed under reduced pressure. The residue was subjected to column chromatography on silica gel (developing solvent, hexane: ethyl acetate=50:1) to obtain 3.41 g of desired 6-phenoxy-2-pyridylmethyl 2,2-dimethylbutyl ether [present compound (17)] as an oily product.

$^1$H-NMR data (solvent, CDCl$_3$; internal standard, TMS): $\delta$ (ppm) 0.80 (bt, 3H), 0.91 (s, 6H), 1.19–1.54 (s, 2H), 3.22 (s, 2H), 4.50 (s, 2H), 6.55–7.80 (m, 8H).

PRODUCTION EXAMPLE 9 PRODUCTION OF PRESENT COMPOUND (35) BY Method A

Under a nitrogen atmosphere, 3.83 g of a 45% aqueous sodium hydroxide solution, 120 mg of tetrabutylammonium bromide and 5 ml of toluene were mixed, and to the resulting mixture solution, a solution of 1.0 g of 2-ethyl-2-methylbutanol and 1.51 g of 6-phenoxy-2-chloromethylpyridine in 5 ml of toluene was added at room temperature. After stirring at room temperature for 16 hours, the reaction solution was poured into dilute hydrochloric acid-ice water and extracted twice with toluene. The toluene layers were combined, washed with a saturated aqueous sodium chloride solution and dried over anhydrous magnesium sulfate, and the solvent was removed under reduced pressure. The residue was subjected to column chromatography on silica gel (developing solvent, n-hexane: ethyl acetate=50:1) to obtain 1.48 g of desired 6-phenoxy-2-pyridylmethyl 2-ethyl-2-methylbutyl ether [present compound (35)] as a colorless oily product.

$n^{24.5}_D 1.5270$.

$^1$H-NMR data (solvent, CDCl$_3$; internal standard, TMS): $\delta$ (ppm) 0.68–1.00 (m, 9H), 1.15–1.60 (m, 4H), 3.28 (s, 2H), 4.51 (s, 2H), 6.60–7.78 (m, 8H).

PRODUCTION EXAMPLE 10 PRODUCTION OF PRESENT COMPOUND (35) BY Method C 0.76 Gram of phenol was dissolved in 5 ml of xylene, and 0.3 g of sodium hydroxide was added. The reaction solution was heated under reflux for 4 hours while water, a by-product, was removed through a column packed with Molecular Sieves 4A. The reaction solution was cooled to room temperature, and a solution of 1.30 g of 6-chloro-2-pyridylmethyl 2-ethyl-2-methylbutyl ether in 5 ml of xylene and 130 mg of cuprous chloride were added, followed by heating under reflux for 8 hours. After cooling, the reaction solution was poured into dilute hydrochloric acid-ice water and extracted with xylene. The xylene layer was washed with water and dried, and the solvent was removed under reduced pressure. The residue was subjected to column chromatography on silica gel (developing solvent, n-hexane: ethyl acetate=50:1) to obtain 1.22 g of desired 6-phenoxy-2-pyridylmethyl 2-ethyl-2-methylbutyl ether [present compound (35)] as a colorless oily product.

$n^{24.0}_D 1.5272$.

$^1$H-NMR data (solvent, CDCl$_3$; internal standard, TMS): $\delta$ (ppm) 0.69–1.02 (m, 9H), 3.29 (s, 2H), 4.51 (s, 2H).

Some of the compounds produced in the same manner as above will be shown in Table 1.

TABLE 1

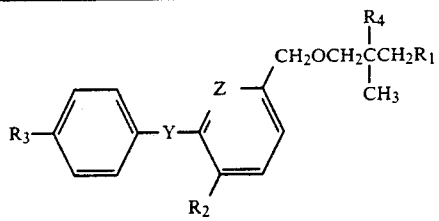

| Compound No. | $R_1$ | $R_2$ | $R_3$ | $R_4$ | Y | Z | Refractive index(°C.) |
|---|---|---|---|---|---|---|---|
| (1) | Cl | H | H | $CH_3$ | O | N | 1.5425 (24.0) |
| (2) | F | H | H | $CH_3$ | O | N | 1.5309 (20.5) |
| (3) | Cl | F | H | $CH_3$ | O | CH | 1.5401 (26.0) |
| (4) | Cl | H | Cl | $CH_3$ | O | N | 1.5466 (25.0) |
| (5) | Cl | F | F | $CH_3$ | O | CH | 1.5342 (24.5) |
| (6) | F | F | H | $CH_3$ | O | CH | 1.5087 (22.5) |
| (7) | Br | H | H | $CH_3$ | O | N | 1.5545 (23.0) |
| (8) | Cl | F | H | $CH_3$ | S | CH | 1.5624 (25.0) |
| (9) | Cl | F | H | $CH_3$ | NH | CH | 1.5529 (24.5) |
| (10) | F | F | H | $CH_3$ | $CH_2$ | CH | 1.5096 (24.5) |
| (11) | Br | F | H | $CH_3$ | O | CH | 1.5522 (25.0) |
| (12) | Br | F | F | $CH_3$ | O | CH | 1.5434 (26.0) |
| (13) | $CH_3$ | F | H | $CH_3$ | O | CH | 1.5100 (25.0) |
| (14) | Cl | F | $CH_3$ | $CH_3$ | O | CH | 1.5411 (24.5) |
| (15) | $CH_3$ | H | Cl | $CH_3$ | O | N | 1.5348 (25.0) |
| (16) | F | F | H | $CH_3$ | O | N | 1.5210 (24.0) |
| (17) | $CH_3$ | H | H | $CH_3$ | O | N | 1.5250 (21.0) |
| (18) | Cl | F | H | $CH_3$ | $CH_2$ | CH | 1.5380 (22.0) |
| (19) | Br | F | $CH_3$ | $CH_3$ | O | N | 1.5504 (25.0) |
| (20) | Cl | F | Br | $CH_3$ | O | CH | 1.5596 (26.0) |
| (21) | Br | F | H | $CH_3$ | $CH_2$ | CH | 1.5463 (24.5) |
| (22) | Br | F | $CH_3$ | $CH_3$ | O | CH | 1.5486 (23.0) |
| (23) | Cl | F | H | $CH_3$ | O | N | 1.5330 (25.0) |
| (24) | $CH_3$ | F | H | $CH_3$ | $CH_2$ | CH | 1.5236 (24.5) |
| (25) | $CH_3$ | F | H | $CH_3$ | S | CH | 1.5576 (26.0) |
| (26) | F | F | H | $CH_3$ | S | CH | 1.5468 (27.0) |
| (27) | $CH_3$ | F | H | $CH_3$ | O | N | 1.5141 (25.0) |
| (28) | $CH_3$ | F | Br | $CH_3$ | O | N | 1.5267 (24.0) |
| (29) | $CH_3$ | F | Br | $CH_3$ | O | CH | 1.5372 (26.0) |
| (30) | $CH_3$ | H | Br | $CH_3$ | O | N | 1.5489 (22.0) |
| (31) | $CH_3$ | H | $C_2H_5$ | $CH_3$ | O | N | 1.5329 (23.0) |
| (32) | Cl | F | $C_2H_5$ | $CH_3$ | O | CH | 1.5366 (25.5) |
| (33) | $CH_3$ | F | H | $CH_3$ | NH | CH | 1.5454 (26.5) |
| (34) | F | F | H | $CH_3$ | NH | CH | 1.5310 (27.0) |
| (35) | $CH_3$ | H | H | $C_2H_5$ | O | N | 1.5270 (24.5) |
| (36) | $CH_3$ | F | H | $C_2H_5$ | NH | CH | 1.5481 (27.0) |
| (37) | $CH_3$ | F | H | $C_2H_5$ | O | CH | 1.5134 (24.5) |
| (38) | Cl | H | H | $C_2H_5$ | O | N | 1.5439 (26.0) |
| (39) | F | H | H | $C_2H_5$ | O | N | 1.5339 (25.0) |
| (40) | $CH_3$ | H | Cl | $C_2H_5$ | O | N | 1.5382 (24.0) |
| (41) | $CH_3$ | H | H | $C_3H_7$ | O | N | 1.5307 (25.0) |
| (42) | $CH_3$ | F | H | $C_3H_7$ | NH | CH | 1.5510 (25.0) |
| (43) | $CH_3$ | F | H | $C_2H_5$ | O | N | 1.5209 (26.0) |
| (44) | Cl | F | H | $C_2H_5$ | NH | CH | 1.5566 (26.0) |
| (45) | Cl | F | H | $C_2H_5$ | O | CH | 1.5422 (26.5) |
| (46) | F | F | H | $C_2H_5$ | NH | CH | 1.5371 (24.0) |
| (47) | F | F | H | $C_2H_5$ | O | CH | 1.5092 (25.0) |

Next, formulation examples will be shown. The present compounds are shown by Compound Nos. described in Table 1, and parts are by weight.

FORMULATION EXAMPLE 1

0.2 Part of each of the present compounds (1) to (47), 2 parts of xylene and 97.8 parts of kerosene are mixed to obtain an oil spray of each compound.

FORMULATION EXAMPLE 2

Ten parts of each of the present compounds (1) to (47), 14 parts of polyoxyethylene styrylphenyl ether, 6 parts of calcium dodecylbenzenesulfonate and 70 parts of xylene are well mixed to obtain an emulsifiable concentrate of each compound.

FORMULATION EXAMPLE 3

Twenty parts of each of the present compounds (1), (3), (13), (17), (33) and (35), 10 parts of fenitrothion, 3 parts of calcium lignosulfonate, 2 parts of sodium lauryl sulfate and 65 parts of synthetic hydrated silicon dioxide are well pulverized and mixed to obtain a wettable powder of each compound.

FORMULATION EXAMPLE 4

One part of each of the present compounds, (1), (2), (6), (8), (10), (34) and (36), 2 parts of carbaryl, 87 parts of kaolin clay and 10 parts of talc are well pulverized and mixed to obtain a dust of each compound.

FORMULATION EXAMPLE 5

Five parts of each of the present compounds (1), (2), (17), (33) and (37), 1 part of synthetic hydrated silicon dioxide, 2 parts of calcium lignosulfonate, 30 parts of bentonite and 62 parts of kaolin clay are well pulverized and mixed, well kneaded with water, granulated and then dried to obtain a granule of each compound.

FORMULATION EXAMPLE 6

0.05 Part of each of the present compounds (1), (3), (6), (13), (34) and (38), 0.2 part of tetramethrin, 0.05 part of resmethrin, 7 parts of xylene and 32.7 parts of deodorized kerosene are well mixed into a solution. The solution is filled in an aerosol container, and after mounting a valve portion on the container, 60 parts of a propellant (liquefied petroleum gas) is charged therein under pressure through the valve portion to obtain an aerosol of each compound.

FORMULATION EXAMPLE 7

To 0.3 g of each of the present compounds (1), (6) and (47) is added 0.3 g of the d-trans-chrysanthemate of allethrin, and the resulting mixture is dissolved in 20 ml of methanol. This solution and 99.4 g of a mosquito coil carrier, which is a 3:5:1 mixture of Tabu power, Pyrethrum marc and wood powder, are uniformly mixed with stirring. After vaporizing methanol, 150 ml of water is added to the residue, and the mixture is well kneaded, shaped and dried to obtain a mosquito coil of each compound.

Next, the usefulness of the present compounds as an active ingredient for insecticides will be shown with reference to the following test examples. The present compounds are shown by Compound Nos. described in Table 1, and compounds used as a control are shown by Compound symbols described in Table 2.

TABLE 2

| Compound symbol | Structural formula | Remark |
|---|---|---|
| (A) | 2-sec-butylphenyl N-methylcarbamate structure with –OC(O)NHCH₃ | BPMC (commercial insecticide) |
| (B) | $(CH_3O)_2P(S)-SCHCOOC_2H_5$ with $CH_2COOC_2H_5$ branch | Malathion (commercial insecticide) |
| (C) | biphenyl-CH₂-O-CH₂-C(CH₃)₃ structure | Compound described in BP No. 1,570,982. |
| (D) | phenoxy-pyridine-CH₂-O-CH₂-C(CH₃)₂Cl structure | Compound described in U.S. Pat. No. 4,664,698. |
| (E) | phenoxy-pyridine-CH₂-O-CH₂-C(CH₃)₃ structure | Same as above. |

TEST EXAMPLE 1

On the bottom of a polyethylene cup of 5.5 cm in diameter was put a filter paper of the same size as the bottom.

Then, 0.7 ml of each of the 200-fold aqueous dilute solutions (active ingredient concentration, 500 ppm) of the emulsifiable concentrates prepared from the following present compounds according to formulation example 2 was dropped down to the filter paper, and 30 mg of sucrose was uniformly scattered as a bait. Thereafter, 10 female adults of housefly (*Musca domestica*) were liberated in the cup which was then covered with a lid. After 24 hours, the dead and alive were examined to obtain mortality. This test was repeated twice.

The results are shown in Table 3.

TABLE 3

| Test compound | Mortality (%) | Test compound | Mortality (%) |
|---|---|---|---|
| (1) | 100 | (10) | 100 |
| (2) | 100 | (11) | 100 |
| (3) | 100 | (12) | 100 |
| (4) | 100 | (13) | 100 |
| (5) | 100 | (14) | 100 |
| (6) | 100 | (15) | 100 |
| (7) | 100 | (16) | 100 |
| (8) | 100 | (17) | 100 |
| (9) | 100 | (18) | 100 |
| (19) | 100 | (34) | 100 |
| (20) | 100 | (35) | 100 |
| (21) | 100 | (36) | 100 |
| (22) | 100 | (37) | 100 |
| (23) | 100 | (38) | 100 |
| (24) | 100 | (39) | 100 |
| (25) | 100 | (40) | 100 |
| (26) | 100 | (41) | 100 |
| (27) | 100 | (42) | 100 |
| (28) | 100 | (43) | 100 |
| (29) | 100 | (44) | 100 |
| (30) | 100 | (45) | 100 |
| (31) | 100 | (46) | 100 |
| (32) | 100 | (47) | 100 |
| (33) | 100 | No treatment | 0 |

TEST EXAMPLE 2

Rice stems of about 12 cm in length were dipped for 1 minute in each of the 6670-fold aqueous dilute solutions (active ingredient concentration, 15 ppm) of the emulsifiable concentrates prepared from the following present compounds and controls according to Formulation example 2. After air-drying, the rice stems were put in a test tube, and ten adults of green rice leafhopper (*Nephotettix cincticeps*) of a resistant strain were liberated in the tube. After one day, the dead and alive were examined to obtain mortality. This test was repeated twice.

The results are shown in Table 4.

TABLE 4

| Test compound | Mortality (%) | Test compound | Mortality (%) |
|---|---|---|---|
| (1) | 100 | (36) | 100 |
| (2) | 100 | (37) | 100 |
| (3) | 100 | (38) | 100 |
| (6) | 100 | (43) | 100 |
| (9) | 100 | (44) | 100 |

TABLE 4-continued

| Test compound | Mortality (%) | Test compound | Mortality (%) |
| --- | --- | --- | --- |
| (13) | 100 | (45) | 100 |
| (16) | 100 | (46) | 100 |
| (17) | 100 | (47) | 100 |
| (23) | 100 | (A) | 5 |
| (27) | 100 | (B) | 0 |
| (33) | 100 | (C) | 0 |
| (34) | 100 | (D) | 50 |
| (35) | 100 | No treatment | 5 |

TEST EXAMPLE 3

Rice stems of about 12 cm in length were dipped for 1 minute in each of the 6670-fold aqueous dilute solutions (active ingredient concentration, 15 ppm) of the emulsifiable concentrates prepared from the following present compounds and controls according to Formulation example 2. After air-drying, the rice stems were put in a test tube, and ten adults or brown planthopper (*Nilaparvata lugens*) were liberated in the tube. After one day, the dead and alive were examined to obtain mortality. This test was repeated twice.

The results are shown in Table 5.

TABLE 5

| Test compound | Mortality (%) | Test compound | Mortality (%) |
| --- | --- | --- | --- |
| (1) | 100 | (33) | 100 |
| (2) | 100 | (34) | 100 |
| (3) | 100 | (35) | 100 |
| (6) | 100 | (36) | 100 |
| (9) | 100 | (43) | 100 |
| (13) | 100 | (44) | 100 |
| (16) | 100 | (46) | 100 |
| (17) | 100 | (C) | 0 |
| (23) | 100 | (D) | 10 |
| (27) | 100 | No treatment | 5 |

TEST EXAMPLE 4

The 1000-fold aqueous dilute solutions (active ingredient concentration, 100 ppm) of the emulsifiable concentrates prepared from the following present compounds and controls according to Formulation example 2 were each sprayed onto rice plants cultivated in polyethylene cups at a rate of 20 ml/2 pots. After air-drying, the pots were covered with wire cages, and the adults of smaller brown planthopper (*Laodelphax striatellus*) were liberated in the cages at a rate of about 15 adults/pot. After one day, the dead and alive were examined to obtain mortality. This test was repeated twice.

The results are shown in Table 6.

TABLE 6

| Test compound | Mortality (%) |
| --- | --- |
| (1) | 100 |
| (17) | 100 |
| (35) | 100 |
| (D) | 55 |
| (E) | 45 |
| No treatment | 3 |

What is claimed is:

1. An ether compound of the formula

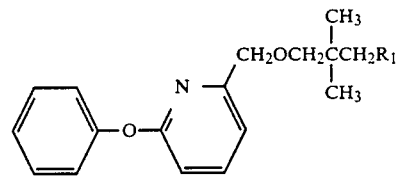

wherein $R_1$ represents halogen or methyl.

2. A compound of the formula

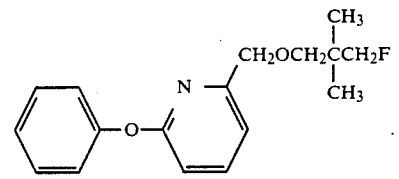

3. A compound of the formula,

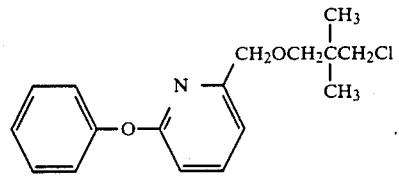

4. A compound of the formula,

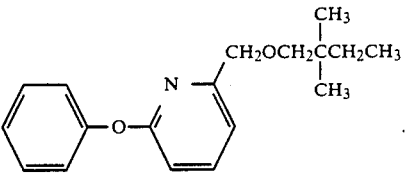

5. An insecticidal composition which comprises as an active ingredient an insecticidally effective amount of the ether compound according to claim 1 and an inert carrier.

6. A method for controlling insects which comprises administering an insecticidally effective amount of the ether compound according to claim 1 to the insects.

* * * * *